United States Patent [19]

Azuma et al.

[11] Patent Number: 4,595,752

[45] Date of Patent: Jun. 17, 1986

[54] PROCESS FOR PREPARING 5,6,7,8-TETRAHYDRO-6-(L-ERYTHRO-1',2'-DIHYDROXYPROPYL)PTERIN

[75] Inventors: Masaaki Azuma; Takehisa Ohashi, both of Kobe; Kiyoshi Watanabe, Akashi, all of Japan

[73] Assignee: Kanegafuchi Kagaku Kogyo Kabushiki Kaisha, Osaka, Japan

[21] Appl. No.: 703,976

[22] Filed: Feb. 21, 1985

[30] Foreign Application Priority Data

Feb. 23, 1984 [JP] Japan .................................. 59-33839

[51] Int. Cl.$^4$ ........................................... C07D 475/04
[52] U.S. Cl. .................................................. 544/258
[58] Field of Search ....................................... 544/258

[56] References Cited

U.S. PATENT DOCUMENTS 2,741,608 4/1956 Shive ..................................... 544/258
4,540,783 9/1985 Viscontini ............................ 544/258

FOREIGN PATENT DOCUMENTS 0079574 5/1983 European Pat. Off. ............. 544/258

OTHER PUBLICATIONS

Rylander, "Catalytic Hydrogenation Over Platinum Metals", Academic Press (1967), pp. 1–5.
"Helvetica Chim. Acta" 61, 2731 (1978).

*Primary Examiner*—Donald G. Daus
*Assistant Examiner*—Robert Benson
*Attorney, Agent, or Firm*—Armstrong, Nikaido, Marmelstein & Kubovcik

[57] ABSTRACT

A process for preparing tetrahydrobiopterin which is rich in the (6R)-form, which comprises hydrogenating L-erythrobiopterin in a basic medium in the presence of a platinum group catalyst. According to the process, tetrahydrobiopterin improved in (6R)/(6S) ratio can be easily obtained in the high yield.

17 Claims, 2 Drawing Figures

PROCESS FOR PREPARING 5,6,7,8-TETRAHYDRO-6-(L-ERYTHRO-1',2'-DIHYDROXYPROPYL)PTERIN

BACKGROUND OF THE INVENTION

The present invention relates to a process for preparing 5,6,7,8-tetrahydro-6-(L-erythro-1',2'-dihydroxypropyl)pterin (hereinafter referred to as "tetrahydrobiopterin"), and more particularly to a process for preparing tetrahydrobiopterin which is rich in the (6R)-form, which comprises catalytically hydrogenating 6-(L-erythro-1',2'-dihydroxypropyl)pterin (hereinafter referred to as "L-erythrobiopterin").

In a living body, it has been well known that (6R)-tetrahydrobiopterin has a very important role as a coenzyme in a catecholamine-serotonin synthesis. Recently, the importance of (6R)-tetrahydrobiopterin has been recognized in the course of the fundamental study thereon. It has been expected that (6R)-tetrahydrobiopterin can be widely used for treatment of patients with Parkinson's disease or depression as well as phenylketonuria which has been conventionally treated with (6R)-tetrahydrobiopterin.

In general, (6R)-tetrahydrobiopterin is synthesized by catalytically hydrogenating L-erythrobiopterin. In accordance with a conventional reaction condition, however, the desired (6R)-form is low in yield and it is difficult to purify, since the (6S)-form which does not exist in nature is by-produced at about 50% of the (6R)-form.

For instance, in Matsuura, "Tanpakushitsu Kakusan Koso" 26, 1394(1981), there is proposed a process in which tetrahydrobiopterin is prepared by catalytically hydrogenating L-erythrobiopterin in 1M hydrochloric acid in the presence of a platinum oxide catalyst. According to the above process, a tetrahydrobiopterin mixture having a (6R)/(6S) ratio (a ratio of the (6R)-form to the (6S)-form of tetrahydrobiopterin, hereinafter the same) of at most 2.23 can only be obtained.

In B. Schircks, J. H. Bieri and M. Viscontini, "Helvetica Chim. Acta" 61, 2731 (1978), there is also proposed a process in which tetrahydrobiopterin is prepared by catalytically hydrogenating L-erythrobiopterin in trifluoroacetic acid in the presence of a platinum oxide catalyst. According to the process, only a tetrahydrobiopterin mixture having a (6R)/(6S) ratio of at most about 2 can be obtained.

As mentioned above, according to the conventional processes the resulting tetrahydrobiopterin mixture has a (6R)/(6S) ratio of at most about 2. Therefore, it (6R)-tetrahydrobiopterin of the natural type is prepared in a high yield on an industrial scale, it is necessary to increase the (6R)/(6S) ratio of a tetrahydrobiopterin mixture. Further, when tetrahydrobiopterin is industrially prepared according to the conventional processes, there is a problem in that an acid stable hydrogenation apparatus is required.

As aforementioned, there have not yet been established any process for industrially preparing (6R)-tetrahydrobiopterin.

An object of the present invention is to provide a process for preparing tetrahydrobiopterin which has an improved (6R)/(6S) ratio, i.e. being rich in (6R)-form of the natural type.

SUMMARY OF THE INVENTION

According to the present invention, tetrahydrobiopterin having the formula (II):

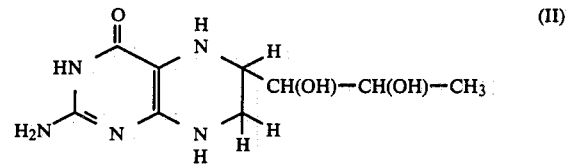
(II)

which is rich in the (6R)-form is prepared by hydrogenating L-erythrobiopterin having the formula (I):

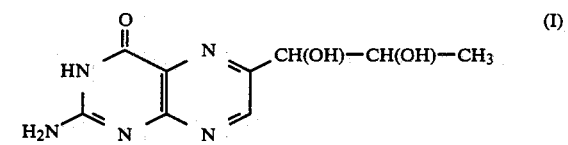
(I)

in a basic medium in the presence of a platinum group catalyst. Tetrahydrobiopterin prepared according to the present invention has an improved (6R)/(6S) ratio of 6 to 9.

BRIEF DESCRIPTION OF THE DRAWINGS

In FIGS. 1 and 2, the indications of "6-(R)-" and "6-(S)-" show the peaks of (6R)-tetrahydrobiopterin and (6S)-tetrahydrobiopterin, respectively.

DETAILED DESCRIPTION

Figure 2:
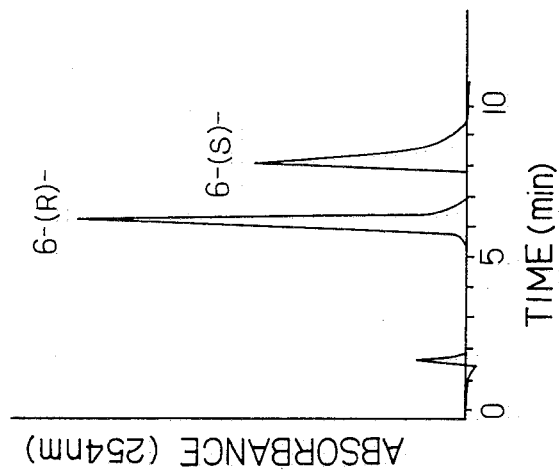
FIG. 2 is a chart of high performance liquid chromatography of tetrahydrobiopterin prepared in Comparative Example 1.

As the basic medium used in the invention, there can be employed an aqueous solution of an alkali metal salt of a weak acid, an aqueous solution of an alkali metal hydroxide, an aqueous solution of an alkaline earth metal hydroxide, or the like.

Examples of the alkali metal salt of a weak acid are, for instance, sodium carbonate, potassium carbonate, sodium acetate, potassium acetate, sodium hydrogencarbonate, potassium hydrogencarbonate, sodium borate, potassium borate, lithium carbonate, lithium acetate, and the like. A preferable salt is sodium carbonate or potassium carbonate.

It is preferable that the amount of the salt is 0.05 to 50% by weight (hereinafter referred to as "%") to water, more preferably 0.1 to 20%. When the amount of the salt is outside the above range, the (6R)/(6S) ratio is low.

Examples of the alkali metal hydroxide employed in the invention are, for instance, sodium hydroxide, potassium hydroxide, and the like. The amount of alkali metal hydroxide is not particularly limited if the alkali metal hydroxide cannot dissolve the platinum group catalyst, and is preferably 0.01 to 5.0% to water, more preferably 0.02 to 1.0%.

Examples of the alkaline earth metal hydroxide employed in the invention are, for instance, calcium hydroxide, barium hydroxide, and the like. It is preferable that an amount of the alkaline earth metal hydroxide is 0.01 to 5.0% to water, more preferably 0.02 to 1.0%.

In the basic medium L-erythrobiopterin is dissolved. It is preferable that the concentration of L-erythrobiopterin in the basic medium is 0.1 to 20%, more preferably 0.2 to 10%. Though it is easy to dissolve L-erythrobiopterin in the basic medium, at the beginning of the reaction L-erythrobiopterin can exist in a solid form in the system. In such a case, L-erythrobiopterin can be gradually dissolved in the basic medium as the reaction proceeds.

Examples of the platinum group catalyst employed in the invention are, for instance, platinum oxide, platinum black, palladium oxide, palladium black, rhodium oxide, and the like, which may be carried on carbon or cotton such as platinum carbon or palladium carbon. The amount of the platinum catalyst is not particularly limited, and is preferably 0.1 to 50% to the whole amount of the system, more preferably 1 to 25%.

The suitable reaction temperature is 0° to 50° C. It is preferable that the reaction is carried out at normal pressure for ease of operation. However, the reaction can also be carried out under more than 1 atm.

The hydrogenation of L-erythrobiopterin can be almost quantitatively. Accordingly, the completion of the reaction can be determined by observing the consumption of a theoretical amount of hydrogen.

After the completion of the reaction, tetrahydrobiopterin hydrochloride improved in the (6R)/(6S) ratio can be easily obtained in a high yield by acidifying the reaction mixture with hydrochloric acid, desalting with an alcohol such as ethanol, and adding a non-solvent such as an alcohol.

Further, it is possible to isolate the (6R)-form by fractional crystallization of the hydrochloride.

The present invention is more specifically described and explained by means of the following Examples, in which all % is by weight unless otherwise noted. It is to be understood that the present invention is not limited to the Examples, and various changes and modifications may be made in the invention without departing from the spirit and scope thereof.

EXAMPLE 1

Figure 1:
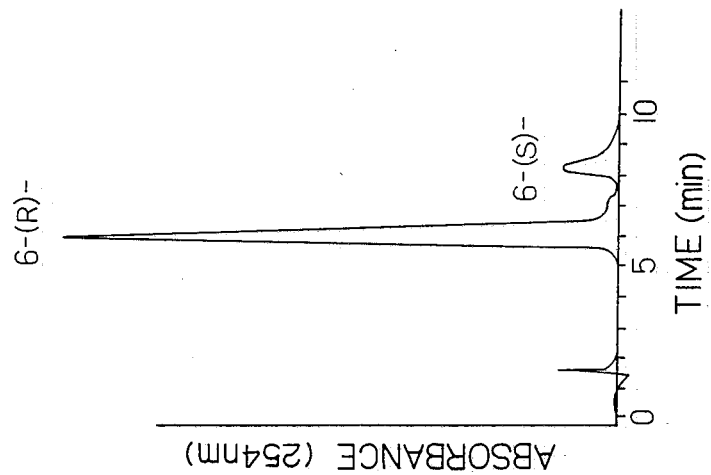
FIG. 1 is a chart of high performance liquid chromatography (hereinafter referred to as "HPLC") of tetrahydrobiopterin prepared in Example 1.

Ten milligrams of platinum oxide was dispersed into 10 ml of a 10% aqueous solution of potassium carbonate, and then hydrogen gas passed through the resulting dispersion with agitation to activate the catalyst. After the completion of the activation (completion of the absorption of hydrogen), 50 mg of purified L-erythrobiopterin dissolved in 10 ml of a 10% aqueous solution of potassium carbonate was added to the above dispersion. The hydrogenation was conducted by agitating the resulting mixture for 10 hours under normal temperature and normal pressure while supplying hydrogen. The end of consumption of hydrogen gas was confirmed by observing the scale of a gas burette. After the completion of the reaction, the catalyst was filtered off from the reaction mixture. The filtrate was acidified with hydrochloric acid, and the resulting filtrate was analyzed by HPLC (column: Whatman partisil 10 SCX 4×250 mm; eluent: 30 mM-$NH_4H_2PO_4$($H_3PO_4$), pH 3.0). The (6R)/(6S) ratio of tetrabiopterin thus obtained was 6.4. The chart of HPLC is shown in FIG. 1.

After the above analyzed filtrate was concentrated under reduced pressure, ethanol was added to the concentrated filtrate, and then the inorganic salt thus deposited was filtered off. The filtrate was concentrated until the precipitate of tetrahydrobiopterin dehydrochloride was obtained. The precipitation was promoted by adding ethanol and the precipitate was collected by filtration to give tetrahydrobiopterin dihydrochloride (yield: 55 mg).

As a result of analyzing by HPLC in the above-mentioned manner, the (6R)/(6S) ratio of the product was found to be 6.0.

EXAMPLE 2

Five milligrams of platinum oxide was dispersed into 5 ml of a 10% aqueous solution of sodium carbonate, and then hydrogen gas passed through the resulting dispersion with agitation to activate the catalyst. And 100 mg of the purified L-erythrobiopterin dissolved in 10 ml of a 10% aqueous solution of sodium carbonate was added to the above dispersion. The hydrogenation was conducted by agitating the resulting mixture for 20 hours under normal temperature and normal pressure while supplying hydrogen. The end of consumption of hydrogen gas was confirmed. After the completion of the reaction, the catalyst was filtered off from the reaction mixture. The filtrate was acidified with hydrochloric acid, and the resulting filtrate was analyzed by HPLC in the same manner as in Example 1. The (6R)/(6S) ratio of tetrahydrobiopterin thus obtained was 6.0.

EXAMPLE 3

Ten milligrams of platinum oxide was dispersed into 10 ml of a 10% aqueous solution of potassium acetate, and then hydrogen gas passed through the resulting dispersion with agitation to activate the catalyst. And 100 mg of the purified L-erythrobiopterin suspensed in 10 ml of a 10% aqueous solution of potassium acetate was added to the above dispersion. The mixture was agitated for 5 hours under normal temperature and normal pressure, L-erythrobiopterin was dissolved to give a light yellow solution in which platinum was dispersed. Further the solution was agitated for 10 hours, and the catalyst was filtered off from the reaction mixture. The filtrate was acidified with hydrochloric acid, and the acidified filtrate was analyzed by HPLC in the same manner as in Example 1. The (6R)/(6S) ratio of tetrahydrobiopterin thus obtained was 6.2.

EXAMPLE 4

Twenty milligrams of platinum oxide was dispersed into 10 ml of water, and then hydrogen gas passed through the resulting dispersion with agitation to activate the catalyst. And 100 mg of the purified L-erythrobiopterin dissolved in 5 ml of a 0.01N aqueous solution of potassium hydroxide was added to the above dispersion. The hydrogenation was conducted by agitating the resulting mixture for 20 hours under normal temperature and normal pressure. After the completion of the reaction the catalyst was filtered off from the reaction mixture. The filtrate was acidified with hydrochloric acid, and the resulting filtrate was analyzed by HPLC in the same manner as in Example 1. The (6R)/(6S) ratio of tetrahydrobiopterin thus obtained was 6.0.

EXAMPLE 5

Twenty milligrams of palladium oxide was dispersed into 10 ml of a 5% aqueous solution of potassium carbonate, and then hydrogen gas passed through the resulting dispersion with agitation to activate the catalyst. And 100 mg of the purified L-erythrobiopterin dissolved in 10 ml of a 5% aqueous solution of potassium carbonate was added to the above dispersion. The hydrogenation was conducted by agitating the resulting mixture for 30 hours under normal temperature and normal pressure. After the completion of the reaction the catalyst was filtered off from the reaction mixture. The filtrate was acidified with hydrochloric acid, and the resulting filtrate was analyzed by HPLC in the same manner as in Example 1. The (6R)/(6S) ratio of tetrahydrobiopterin thus obtained was 6.7.

EXAMPLE 6

Ten milligrams of platinum oxide was dispersed into 10 ml of a 1% aqueous solution of lithium carbonate, and then the hydrogen gas passed through the resulting dispersion with agitation to activate the catalyst. And 50 mg of the purified L-erythrobiopterin in 10 ml of a 1% aqueous solution of lithium carbonate was added to the above dispersion. The hydrogenation was conducted by agitating the resulting mixture for 15 hours at room temperature. After the completion of the reaction the catalyst was filtered off from the reaction mixture. The filtrate was acidified with hydrochloric acid, and the resulting filtrate was analyzed by HPLC in the same manner as in Example 1. The (6R)/(6S) ratio of tetrahydrobiopterin thus obtained was 5.6.

EXAMPLE 7

Ten milligrams of platinum black was dispersed into 10 ml of a 10% aqueous solution of potassium carbonate, and then hydrogen gas passed through the resulting dispersion with agitation to activate the catalyst. And 50 mg of the purified L-erythrobiopterin in 10 ml of a 10% aqueous solution of potassium carbonate was added to the above dispersion. The hydrogenation was conducted by agitating the resulting mixture for 17 hours at room temperature. After the completion of the reaction the catalyst was filtered off from the reaction mixture. The filtrate was acidified with hydrochloric acid, and the resulting filtrate was analyzed by HPLC in the same manner as in Example 1. The (6R)/(6S) ratio of tetrahydrobiopterin thus obtained was 9.0.

COMPARATIVE EXAMPLE 1

Ten miligrams of platinum oxide was dispersed into 10 ml of a 0.1N of aqueous solution of hydrochloric acid, and then hydrogen gas passed through the resulting dispersion with agitation to activate the catalyst. And 100 mg of the purified L-erythrobiopterin in 10 ml of a 0.1N aqueous solution of hydrochloric acid was added to the above dispersion. The hydrogenation was conducted by agitating the resulting mixture for 1 hour under normal temperature and normal pressure. After the completion of the reaction, the catalyst was filtered off from the reaction mixture. The resulting filtrate was analyzed by HPLC in the same manner as in Example 1. The (6R)/(6S) ratio of filtrate thus obtained was 1.4. The chart of HPLC is shown in FIG. 2.

COMPARATIVE EXAMPLE 2

Ten milligrams of palladium oxide was dispersed into 10 ml of a 1.0N aqueous solution of hydrochloric acid, and then hydrogen gas passed through the resulting dispersion with agitation to activate the catalyst. And 100 mg of the purified L-erythrobiopterin in 10 ml of a 1.0N aqueous solution of hydrochloric acid was added to the above dispersion. The hydrogenation was conducted by agitating the resulting mixture for 3 hours under normal temperature and normal pressure. After the completion of the reaction the catalyst was filtered off from the reaction mixture. The resulting filtrate was analyzed by HPLC in the same manner as in Example 1. The (6R)/(6S) ratio of filtrate thus obtained was 1.9.

In addition to the ingredients employed in Examples, other ingredients can be employed in Examples as set forth in the specification to obtain substantially the same results.

What we claim is:

1. A process for preparing 5,6,7,8-tetrahydro-6-(L-erythro-1',2'-dihydroxypropyl)pterin having the formula (II):

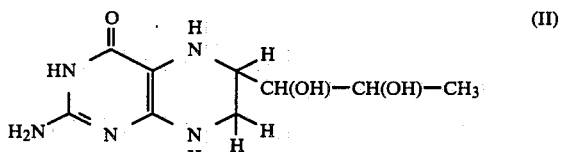

which comprises hydrogenating 6-(L-erythro-1',2'-dihydroxypropyl)pterin having the formula (I):

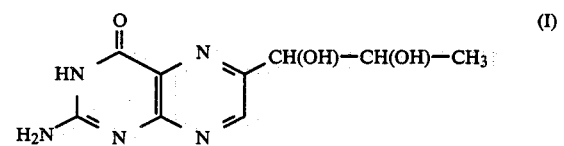

in the presence of a platinum group catalyst in a basic medium selected from the group consisting of an aqueous solution of an alkali metal salt of a weak acid, an aqueous solution of an alkali metal hydroxide, an aqueous solution of calcium hydroxide and an aqueous solution of barium hydroxide to give 5,6,7,8-tetrahydro-6-(L-erythro-1',2'-dihydroxypropyl)pterin of the formula (II) which is rich in the (6R) form.

2. The process of claim 1, wherein said platinum group catalyst is platinum black or platinum oxide.

3. The process of claim 1, wherein said platinum group catalyst is palladium black or palladium oxide.

4. The process of claim 1, wherein said platinum group catalyst is rhodium oxide.

5. The process of claim 1, wherein said platinum group catalyst is platinum carried on carbon or cotton.

6. The process of claim 1, wherein said platinum group catalyst is palladium carried on carbon or cotton.

7. The process of claim 1, wherein said alkali metal salt of weak acid is sodium carbonate or potassium carbonate.

8. The process of claim 1, wherein said alkali metal salt of weak acid is sodium acetate, potassium acetate, sodium hydrogen-carbonate, potassium hydrogencarbonate, sodium boric acid, potassium boric acid, lithium carbonate or lithium acetate.

9. The process of claim 1, wherein said alkali metal hydroxide is sodium hydroxide or potassium hydroxide.

10. The process of claim 1, wherein the amount of said alkali metal salt of a weak acid is 0.05 to 50% by weight to water.

11. The process of claim 1, wherein the amount of said salt is 0.1 to 20% by weight to water.

12. The process of claim 1, wherein the amount of said calcium hydroxide or barium hydroxide is 0.01 to 5.0% by weight to water.

13. The process of claim 1, wherein the amount of said alkaline earth metal hydroxide is 0.02 to 1.0% by weight to water.

14. The process of claim 1, wherein the amount of said alkali metal hydroxide is 0.01 to 5.0% by weight to water.

15. The process of claim 1, wherein the amount of said alkali metal hydroxide is 0.02 to 1.0% by weight to water.

16. The process of claim 1, wherein the concentration of the 6-(L-erythro-1',2'-dihydroxypropyl)pterin is 0.1 to 20% by weight to the basic medium.

17. The process of claim 1, wherein the concentration of the 6-(L-erythro-1',2'-dihydroxypropyl)pterin is 0.2 to 10% by weight to the basic medium.

* * * * *